United States Patent [19]

Wu et al.

[11] Patent Number: 5,461,148
[45] Date of Patent: Oct. 24, 1995

[54] PROCESS FOR PREPARING BENZAZEPINE INTERMEDIATES FOR THE SYNTHESIS OF D1 ANTAGONISTS

[75] Inventors: Guang-Zhong Wu, Somerville; Martin Steinman, Livingston; Yee-Shing Wong, Florham Park, all of N.J.

[73] Assignee: Schering Corporation, Kenilworth, N.J.

[21] Appl. No.: 127,668

[22] Filed: Sep. 27, 1993

[51] Int. Cl.[6] .................... C07D 223/14; C07D 223/16; C07C 217/60
[52] U.S. Cl. .................... 540/576; 540/595; 564/360
[58] Field of Search .................... 540/576, 595; 564/360

[56] References Cited

U.S. PATENT DOCUMENTS

| | | | |
|---|---|---|---|
| 4,638,003 | 1/1987 | Chiarino et al. | 514/255 |
| 4,973,586 | 11/1990 | Berger et al. | 514/217 |
| 5,227,494 | 7/1993 | Schumacher et al. | 548/237 |

OTHER PUBLICATIONS

Berger, et al, *J. Med. Chem.*, 32, 1913–1921 (1989).

*Primary Examiner*—Philip I. Datlow
*Attorney, Agent, or Firm*—Paul A. Thompson

[57] ABSTRACT

Disclosed are a process and intermediates of the formulae

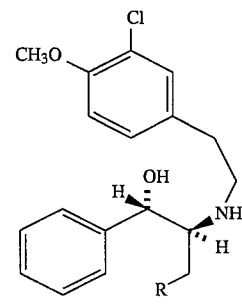

or

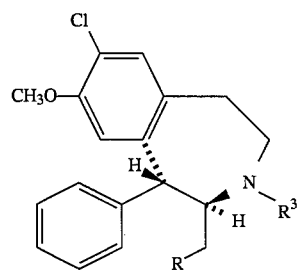

wherein R is —CH$_2$OH or —OH and R$^3$ is H or C$_1$-C$_6$ alkyl; useful for preparing benzazepines of the formula

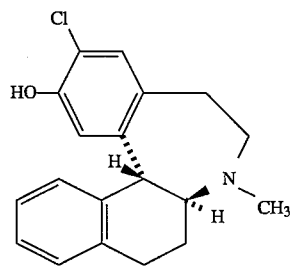

having activity as selective D1 antangonists.

13 Claims, No Drawings

PROCESS FOR PREPARING BENZAZEPINE INTERMEDIATES FOR THE SYNTHESIS OF D1 ANTAGONISTS

BACKGROUND OF THE INVENTION

The present invention relates to a process for preparing intermediates useful in the preparation of benzazepines having activity as selective D1 receptor antagonists.

U.S. Pat. No. 4,973,586 discloses fused benzazepines, and in particular the compound known as SCH 39166, having the structure I

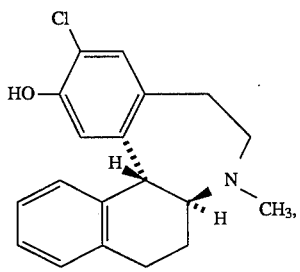

as selective D1 antagonists useful in the treatment of psychoses, depression, pain and D1 dependent neurological disorders. Methods for preparing such compounds are also described therein.

Berger, et al, *J. Med. Chem.*, 32, 1913–1921 (1989), discloses a process for preparing SCH 39166 comprising acid promoted cyclization of a compound of the formula (1) to give a 1:1 mixture of cis and trans benzazepines (cis-2 and trans-2, respectively). Compound trans-2 is then converted to racemic compound II via a multi-step procedure. Compound I[ is resolved via its di-O,O'-p-tolyltartrate salt and hydrolyzed with HBr and HOAc to give SCH 39166 (I).

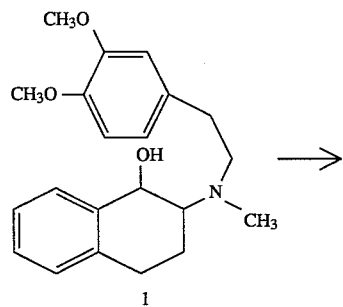

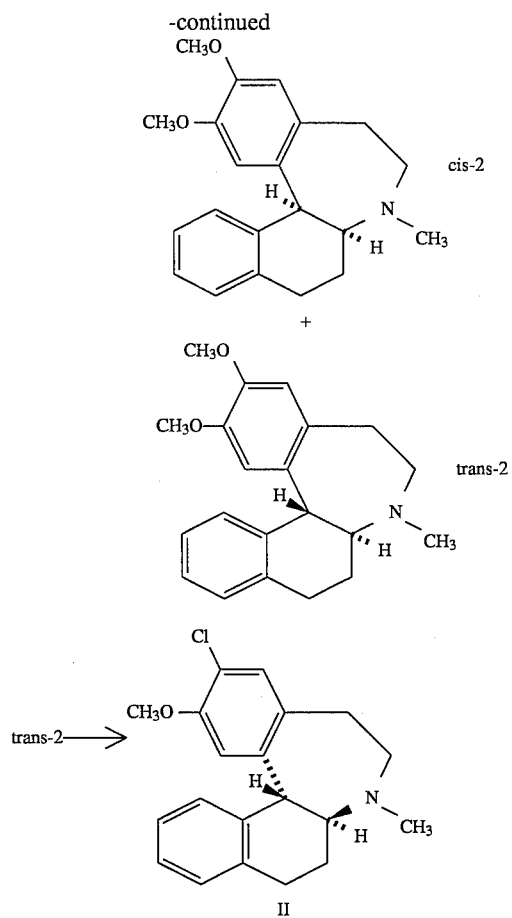

The prior art process suffers from several shortcomings. It is inefficient, producing a 1:1 mixture of cis and trans benzazepines in the cyclization step. In addition conducting the resolution step at a late stage of the synthesis is very costly and adds further inefficiency. Therefore, it was desirable to develop a chemically efficient and cost effective process for preparing SCH 39166 of high optical purity.

SUMMARY OF THE INVENTION

The present invention comprises a process for preparing a compound of the formula I

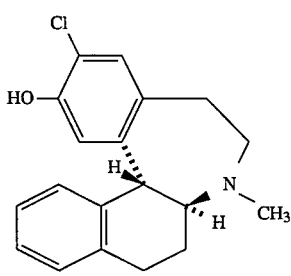

comprising the steps:

(a) regioselectively cyclizing a chiral alcohol of the formula

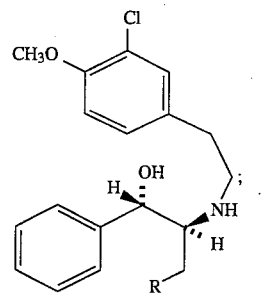

wherein R is —OH or —CH₂OH, to form a compound of the formula

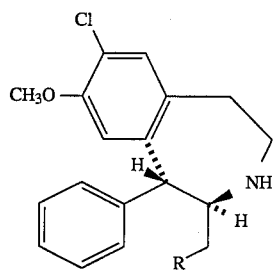

(b) treating the product of Step (a) with formaldehyde and formic acid to form an N-methyl compound of the formula

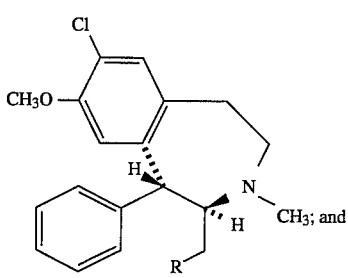

(c) where R is —CH₂OH, reacting the product of step (b) with PCl₅ and AlCl₃; or where R is —OH, converting the product of step (b) to the one carbon homologous product, wherein R is —CH₂OH or —CO₂H, then:

(i) where R is —CH₂OH, reacting the homologous product with PCl₅ and AlCl₃; or (ii) where R is —CO₂H, treating the homologous product with an acid activating agent and a Lewis acid to form a ketone of the formula

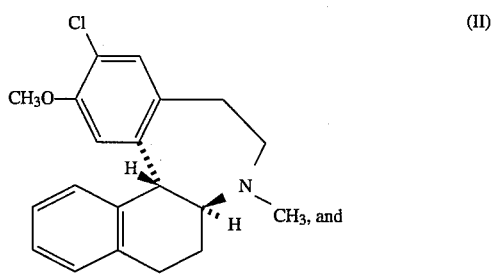

treating the ketone with a hydride reducing agent to form a compound of formula II

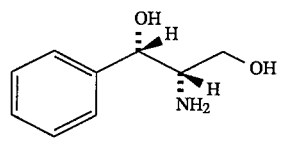  (II)

hydrolyzing the compound of formula II; to form the compound of formula I.

The present invention further comprises a process for preparing compounds of the formula I, designated Process A, wherein the chiral alcohol of step (a), wherein R is —CH₂OH, is prepared by a process comprising the steps:

(A1) treating an (S,S)-amino diol of the formula

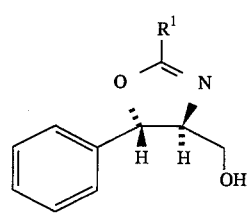

with a nitrile of the formula R¹CN, wherein R¹ is C₁-C₆ alkyl, to form a chiral oxazoline of the formula wherein R¹ is as defined above;

(A2) treating the chiral oxazoline of step (A1) with an activating agent, then with a cyanide salt to form a nitrile of the formula

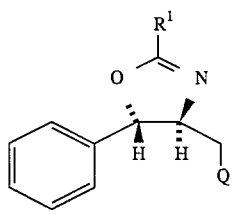

wherein R¹ is as defined above and Q is CN;

(A3) treating the nitrile of step (A2) with HCl and an alcohol of the formula R²OH, wherein R² is $C_1$-$C_6$ alkyl, to form an ester of the formula

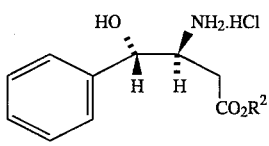

wherein Q is —$CO_2R^2$, then treating the ester with a base and an acid halide of the formula

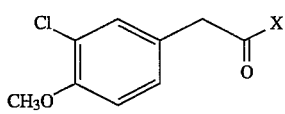

wherein X is Cl or Br, to form a mixture of an ester and a lactone of the formulae

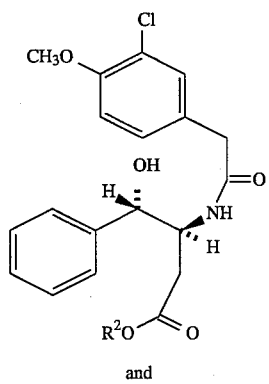

and

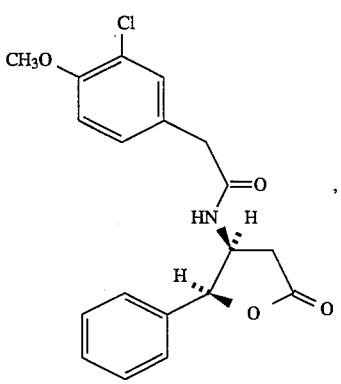

respectively, wherein R² is as defined above;

(A4) treating the ester and lactone mixture of step (A3) with a hydride reducing agent to form the chiral alcohol of step (a), wherein R is —$CH_2OH$.

In an alternative embodiment, the present invention further comprises a process for preparing compounds of the formula I, designated Process B, wherein the chiral alcohol of step (a), wherein R is —OH, is prepared by a process comprising the steps:

(B1) coupling an (S,S)-amino diol of the formula

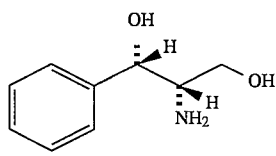

with an acid of the formula

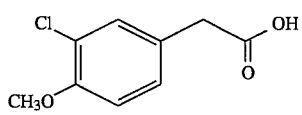

to form an amide of the formula

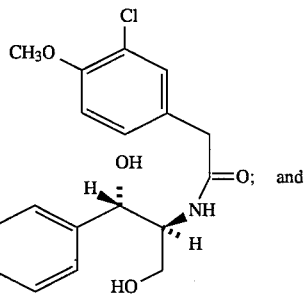

(B2) treating the amide of step (B1) with a hydride reducing agent to form the chiral alcohol of step (a), wherein R is —OH.

The present invention further comprises a process, designated process C, wherein in step (c) the product of step (b), wherein R is —OH, is converted to the one carbon homologous product, wherein R is —$CH_2OH$ or —$CO_2H$ by a process comprising the steps:

(C1) treating the product of step (b) with an activating agent to form a compound of the formula

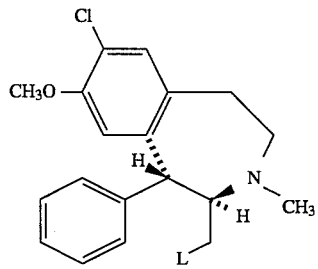

wherein L is a leaving group;

(C2) treating the product of step (C1) with a cyanide salt to form a compound of the formula

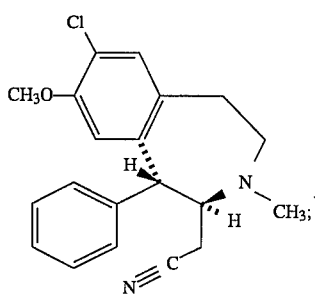

(C3) (i) treating the product of step (C2) with a strong acid and water to form the homologous product wherein R is —CO₂H; or (ii) treating the product of step (C2) with a strong acid and an alcohol of the formula R²OH to form an ester of the formula

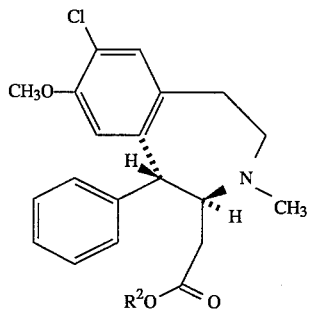

wherein R² is $C_1$-$C_6$ alkyl, and treating the ester with a hydride reducing agent to form the homologous product where R is —CH₂OH.

Preferred is a process as described above wherein: R is —CH₂OH; and the chiral alcohol of step (a) is cyclized by treating with CH₃SO₃H/BF₃, HF/BF₃ or TFA.

Also preferred is a process as described above wherein: R is —OH; the chiral alcohol of step (a) is cyclized by treating with CH₃SO₃H/BF₃, HF/BF₃ or TFA; and in step (c), the product of step (b) is converted to the one carbon homologous product wherein R is —CH₂OH.

Another preferred process is a process as described above wherein: R is —OH; the chiral alcohol of step (a) is cyclized by treating with CH₃SO₃H/BF₃, HF/BF₃ or TFA; and in step (c), the product of step (b) is converted to the one carbon homologous product wherein R is —CO₂H.

Yet another preferred process is a process A as described above wherein: R¹ is CH₃; the activating agent of step (A2) is mesyl chloride or tosyl chloride; the cyanide salt of step (A2) is NaCN, KCN or LiCN; R² is CH₃; X is Cl; and in step (A4) the hydride reducing agent is NaBH₄.

Still another preferred process is a process B as described above wherein: in step (B1) the coupling of the (S,S)-amino diol to the acid is by treating with an acid activating agent or an amide coupling agent; and the hydride reducing agent of step (B2) is NaBH₄.

Also preferred is a process C as described above wherein: the activating agent of step (C1) is mesyl chloride or tosyl chloride; L is OMs or OTs; the cyanide salt of step (C2) is NaCN, KCN or LiCN; the strong acid of step (C3) (i) is H₂SO₄; and in step (C3) (ii), the strong acid of is H₂SO₄, R² is CH₃, and the hydride reducing agent is LiBH₄.

The process of the present invention does not suffer the shortcomings of the prior art processes. It is chemically efficient and, by utilizing inexpensive chiral starting materials produces the chiral product compound I having the correct relative and absolute stereochemistry.

The present invention further comprises a chiral compound of the formula

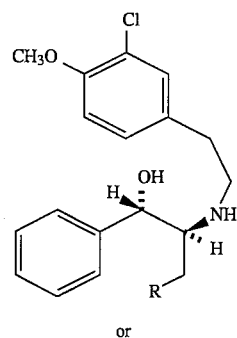

or

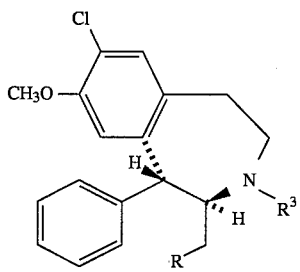

wherein R is —CH₂OH or —OH and R³ is H or $C_1$-$C_6$ alkyl, useful for preparing benzazepines having activity as selective D1 receptor antagonists. Preferably R³ is H or methyl.

DETAILED DESCRIPTION

In general, stereochemical representations are meant to denote absolute stereochemistry and, where more than one chiral center is present, relative stereochemistry. The process of the present invention utilizes optically active starting materials and produces a single enantiomer of compound I. The stereochemical purity of compounds is generally given in terms of the enantiomeric excess (e.e.).

As used herein the term "alkyl" means a straight or branched alkyl chain of 1 to 6 carbon atoms;

"cyanide salt" means a metal cation salt of cyanide anion, preferably NaCN, KCN or LiCN;

"hydride reducing agent" means a metal hydride reagent such as LiAlH₄, NaBH₄, LiBH₄ or NaBH₃CN;

"borane reducing agent" means a stable BH₃ complex capable of reducing a ketone, such as BH₃.S(CH₃)₂;

"strong acid" means a protic acid having a pKa <2, such as H₂SO₄;

"Lewis acid" means a Lewis acid capable of catalyzing a Friedel-Crafts type reaction, such as AlCl₃;

"base" means Na₂CO₃, K₂CO₃, NaHCO₃ or KHCO₃;

"hydroxide base" means an alkali metal hydroxide, such as NaOH, KOH or LiOH, or an alkaline earth metal hydroxide such as Ca(OH)₂;

"tertiary amine base" means a tertiary amine such as triethylamine or di-isopropylethylamine;

"leaving group" means a group which can be readily displaced by a nucleophile, preferably —Cl, —Br, —I, —OSO₂CH₃ (—OMs); —OSO₂CF₃ or —OSO₂C₆H₄CH₃

(—OTs);

"activating agent" means a reagent capable of converting a hydroxy group into a leaving group, preferably mesyl chloride or tosyl chloride;

"acid activating agent" means a reagent capable of converting a carboxylic acid into a reactive derivative such as an acid halide, with preferred reagents being SOCl₂ and oxalyl chloride;

"amide coupling agent" means a reagent capable of effecting the dehydrative coupling of a carboxylic acid and an amine to form an amide, preferably such reagents are carbodiimides used alone of in the presence of HOBT; preferred carbodiimides are DEC and DCC.

As used herein the following reagents and solvents are identified by the abbreviations indicated: para-toluenesulfonyl chloride (tosyl chloride, TsCl); methanesulfonyl chloride (mesyl chloride, MsCl); 1-(3-dimethylaminopropyl)-3-ethylcarbodiimide hydrochloride (DEC); dicyclohexylcarbodiimide (DCC); 1-hydroxybenzotriazole (HOBT); tetrahydrofuran (THF); iso-propanol (i-PrOH); ethanol (EtOH); methanol (MeOH); ethyl acetate (EtOAc); acetic acid (AcOH); tert-butyl methyl ether (t-BuOMe); triethylamine (Et₃N); N,N-dimethylformamide (DMF); trifluoroacetic acid (TFA); dimethylsulfoxide (DMSO).

The present invention comprises a process for preparing a compound of the formula I as shown in Reaction Scheme 1.

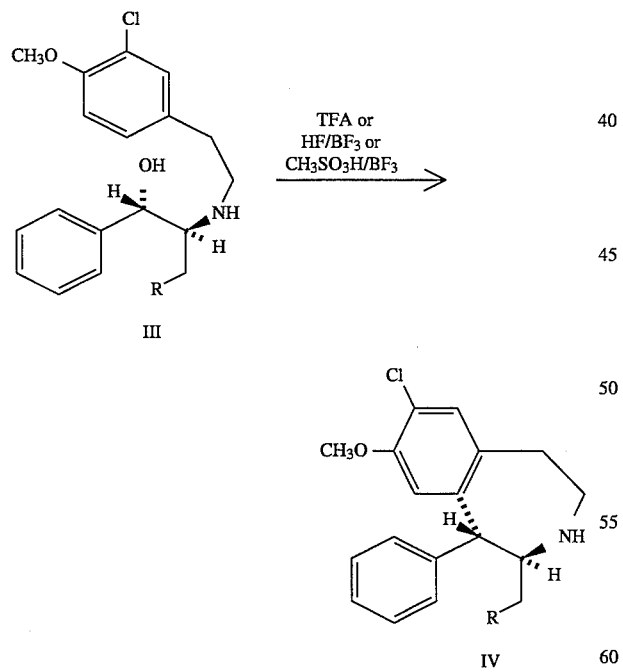

Reaction Scheme 1

Step (a)

Step (b)

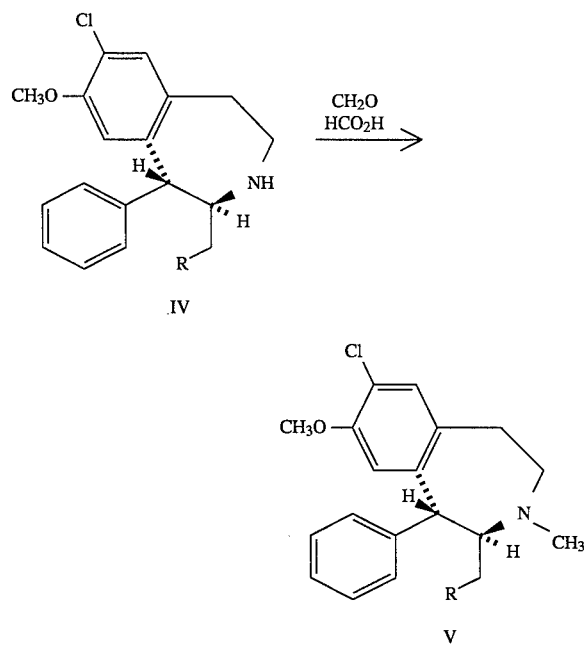

Step (c) (i)

Step (c) (ii)

-continued
Reaction Scheme 1

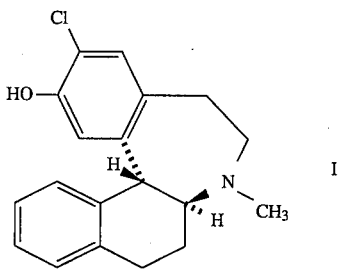

In Scheme 1, Step (a), the chiral alcohol III is combined with $CH_3SO_3H$, at $-20°$ to $+35°$ C., preferably at $0°-20°$ C., then treated with $BF_3$ to form the cyclized product IV.

Alternatively, in Step (a), the chiral alcohol III is combined with HF at $-80°$ to $-20°$ C., preferably at $-78°$ to $-30°$ C., and treated with $BF_3$ to form the cyclized product The cyclization of Step (a) can also be performed by treating the chiral alcohol III with TFA to form the cyclized product IV.

In Step (b), compound IV is reacted with $CH_2O$, preferably 37% aqueous formaldehyde, and formic acid, in a suitable solvent, such as DMF at $60°$ to $140°$ C., preferably at about $100°$ C. to give the N-methyl compound V.

In Step (c) (i), where R is $-CH_2OH$, compound V is treated with $PCl_5$ and $AlCl_3$ in a suitable solvent, such as toluene, at $0°$ to $100°$ C., preferably at $50°$ to $80°$ C., to form compound I.

In Step (c) (ii), where R is $-OH$, compound V is converted to a one carbon homologous product, wherein R is $-CH_2OH$ or $-CO_2H$, which is in turn converted to compound I, via the process described in Reaction Scheme C (below). Where R is $-CH_2OH$, the homologous product is then cyclized as described above for Step (c) (i). Where R is $-CO_2H$, the homologous product is treated with an acid activating agent, such as $SOCl_2$, at $10°$ to $60°$ C., preferably at $30°$ to $50°$ C., then treated with an Lewis acid, such as $AlCl_3$, at $-20°$ to $20°$ C., preferably at $0°$ to $10°$ C., to form a cyclized ketone XVII. The cyclized ketone XVII is treated with a borane reducing agent, such as $BH_3 \cdot S(CH_3)_2$, in a suitable solvent, such as TFA, at $-10°$ to $50°$ C., preferably at $10°$ to $30°$ C., to form a compound of the formula II. The methoxy group of the reduced product II is then hydrolyzed by treating with $BCl_3$, or alternatively, via procedures reported in the prior art, such as by treating with HBr and HOAc via the procedure described by Berger, et al, *J. Med. Chem.*, 32, 1913–1921 (1989), to form a compound of the formula I.

The present invention further comprises a process as described above wherein the chiral alcohol (III) of Step (a), wherein R is $-CH_2OH$, (i.e., a compound of the formula IIIa) is prepared according to Process A, as shown in Reaction Scheme A.

Reaction Scheme A

Step A1

-continued
Reaction Scheme A

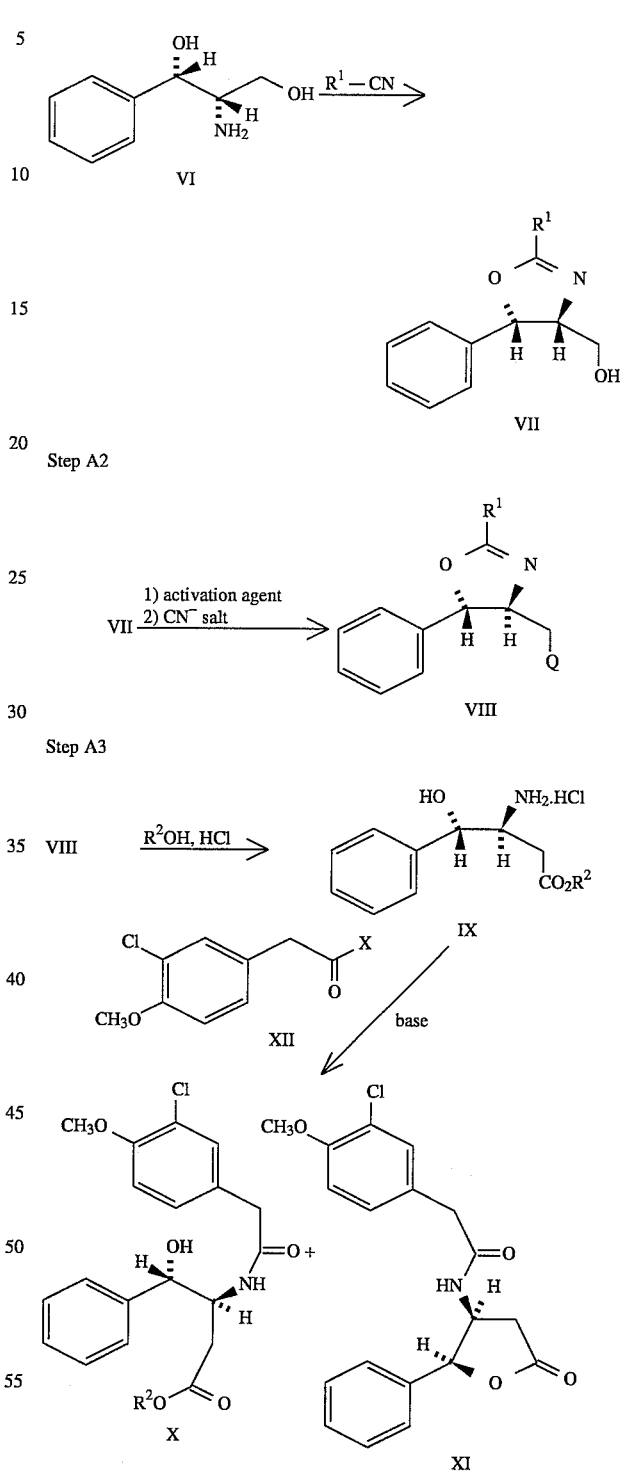

Step A2

Step A3

Step A4

-continued
Reaction Scheme A

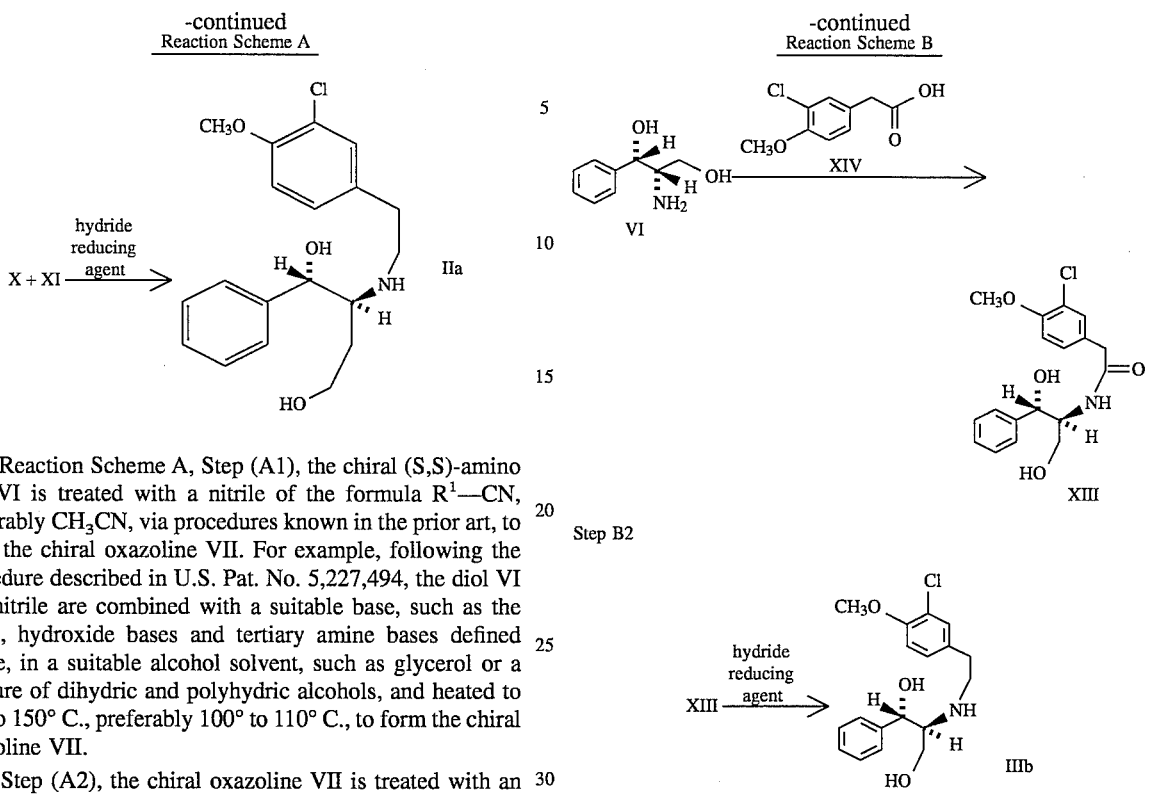

In Reaction Scheme A, Step (A1), the chiral (S,S)-amino diol VI is treated with a nitrile of the formula $R^1$—CN, preferably $CH_3CN$, via procedures known in the prior art, to form the chiral oxazoline VII. For example, following the procedure described in U.S. Pat. No. 5,227,494, the diol VI and nitrile are combined with a suitable base, such as the bases, hydroxide bases and tertiary amine bases defined above, in a suitable alcohol solvent, such as glycerol or a mixture of dihydric and polyhydric alcohols, and heated to 70° to 150° C., preferably 100° to 110° C., to form the chiral oxazoline VII.

In Step (A2), the chiral oxazoline VII is treated with an activating agent, preferably mesyl chloride or tosyl chloride, in a suitable solvent, such as toluene, in the presence of a tertiary amine base, preferably $Et_3N$, at 0° C. to 50° C., preferably at 10° to 20° C, to form an activated intermediate of the formula VIII, wherein Q is a leaving group, preferably OMs or OTs. The activated intermediate is treated with a cyanide salt, preferably NaCN, LiCN or KCN, in a suitable solvent, such as DMSO, at 20° to 100° C., preferably 60° to 80° C., to form the nitrile VIII, wherein Q is CN.

In Step (A3), the nitrile VIII is treated with HCl, preferably concentrated HCl, at 50° to 100° C., preferably about 70° to 80° C., then treated with an alcohol $R^2OH$, wherein $R^2$ is as defined above, and HCl, preferably gaseous HCl, at 0° to 40° C., preferably at 10° to 37° C., to form the ester IX. The ester IX is treated with a base, preferably $NaHCO_3$, $K_2CO_3$ or $Na_2CO_3$, and the acid halide XII, wherein X is Br or Cl, to form a mixture of the ester X and the lactone XI.

In Step (A4), the mixture of X and XI is treated with a hydride reducing agent, preferably $NaBH_4$, and acetic acid in a suitable solvent, such as THF, at −10° to 30° C., preferably 5° to 20° C., then heated to 30° to 100° C., preferably at reflux temperature, to form the chiral alcohol IIIa, i.e., a chiral alcohol of the formula III, wherein R is —$CH_2OH$.

The present invention further comprises a process as described above wherein the chiral alcohol (III) of Step (a), wherein R is —OH, (i.e., a compound of the formula IIIb) is prepared according to Process B, as shown in Reaction Scheme B.

Reaction Scheme B

Step B1

-continued
Reaction Scheme B

Step B2

In Reaction Scheme B, Step (B1), the (S,S)-amino diol VI is coupled to the acid XIV by treating XIV with an acid activating agent, preferably $SOCl_2$ or oxalyl chloride, in a suitable solvent, such as $CH_2Cl_2$, at −10° to 40° C., preferably at 10° to 30° C., then heating at 40° to 80° C., preferably at 50° to 70° C., to form the acid chloride of XIV, i.e., a compound of the formula XII, as defined above, wherein X is Cl. The acid chloride is added to a mixture of VI, a hydroxide base, preferably NaOH or KOH, and water at −10° to 40° C., preferably at 10° to 25° C., to form the amide XIII.

Alternatively in Step (B1), the (S,S)-amino diol VI is coupled to the acid XIV by treating with an amide coupling agent, such as DEC or DCC. The coupling agent is used alone or in the presence of HOBT, and the reaction is carried out in a suitable solvent, such as $CH_2Cl_2$ or a mixture of $CH_2Cl_2$ and DMF, at −20° to 60° C., preferably about 0° to 30° C., to form the amide XIII.

In Step (B2), the amide XIII is treated with a hydride reducing agent, preferably $NaBH_4$, according to the procedure described for Step (A4) in Reaction Scheme A, to give the chiral alcohol IIIb, i.e., a chiral alcohol of the formula III wherein R is —OH.

The present invention further comprises a process as described above wherein the compound V of Step (b), wherein R is —OH, (i.e., a compound of the formula Va) is converted to the one carbon homologous product V, wherein R is —$CH_2OH$ or —$CO_2H$, (i.e., compounds of the formula Vb and Vc, respectively) according to Process C, as shown in Reaction Scheme C.

Reaction Scheme C

Step C1

-continued
Reaction Scheme C

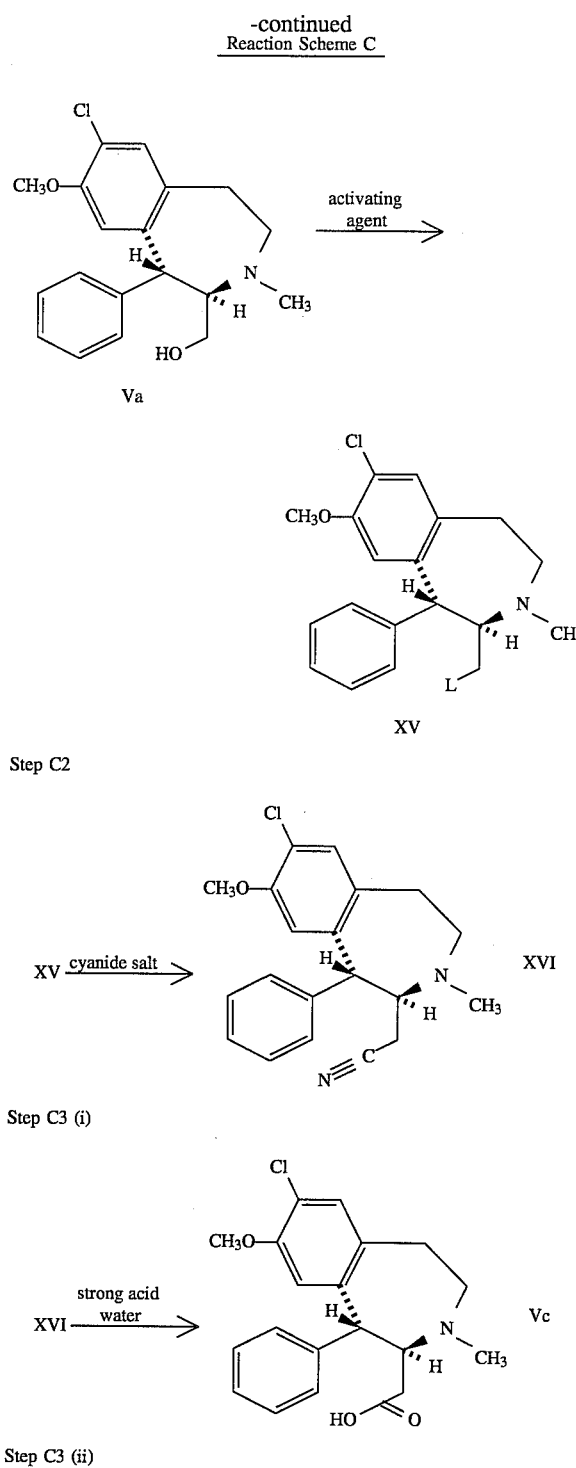

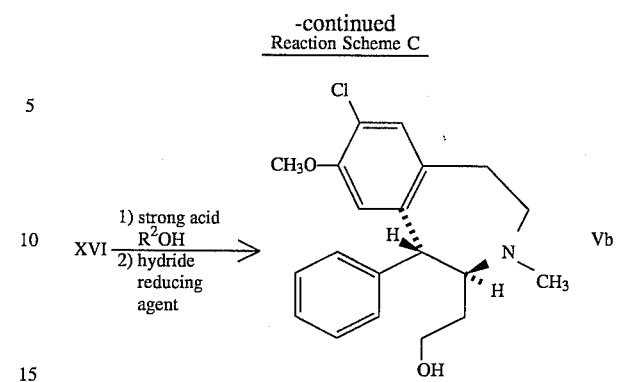

In Reaction Scheme C, Step (C1), compound Va (i.e., a compound of the formula V wherein R is —OH) is treated with an activating agent, preferably mesyl chloride or tosyl chloride, in a suitable solvent, such as toluene or THF, in the presence of a tertiary amine base, such as $Et_3N$, at $-10°$ C. to $25°$ C., preferably at $0°$ to $10°$ C., to form a compound of the formula XV wherein L is a leaving group, preferably OMs or OTs.

In Step (C2), compound XV is treated with a cyanide salt, preferably NaCN, LiCN or KCN, in a suitable solvent, such as DMSO, at $30°$ to $100°$ C., preferably $60°$ to $80°$ C., to form a compound of the formula XVI.

In Step (C3) (i), compound XVI is treated with a strong acid, such as $H_2SO_4$, in a suitable solvent, such as an alcohol/water mixture, preferably methanol/water, at $40°$ to $100°$ C. (the temperature is in part determined by the boiling point of the solvent), preferably $50°$ to $80°$ C., to form a compound of the formula Vc (i.e., a compound of the formula V wherein R is —$CO_2H$).

In Step (C3) (ii), compound XVI is treated with a strong acid. preferably $H_2SO_4$, in an alcohol solvent of the formula $R^2OH$ wherein $R^2$ is as defined above, preferably MeOH, at $30°$ to $100°$ C., preferably at $50°$ to $80°$ C., to form an ester. The ester is treated with a hydride reducing agent, such as $NaBH_4$, in a suitable solvent, such as MeOH or EtOH, at $0°$ to $60°$ C., preferably at $10°$ to $50°$ C., then further treated with $LiBH_4$ in THF at $20°$ to $90°$ C., preferably at $60°$ to $85°$ C., to form a compound of the formula Vb (i.e., a compound of the formula V wherein R is —$CH_2OH$).

Starting compounds of the formula VI, XII and XIV are commercially available or can be prepared via known methods.

The following preparations and examples illustrate the process of this invention:

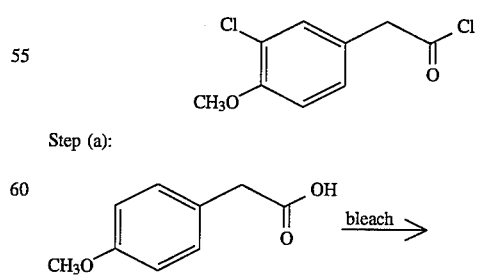

Step (a):

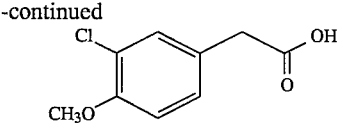

Cool 100 mL of bleach (11% NaOCl) to 5° C., then add 100 g (0.59 mole) of 4omethoxyphenyl acetic acid, keeping the temperature <35° C. Add 24 g (0.3 mole) of 50% NaOH, again keeping the temperature <35° C. Slowly add (dropwise) 1.0 L of bleach, keeping the temperature <35° C. and adding NaOH or 3.0 N $H_2SO_4$ as needed to maintain a pH of 8–11. Stir the resulting mixture at 25° C. for 2 h, then add 50 g of $Na_2SO_3$ and stir at 25° C. for 30 min. Slowly add (dropwise) 300 mL of 5.0 N $H_2SO_4$ to adjust to pH 1 (keep temperature <50° C.), then cool the mixture to 25° C. and stir for 30 min. Filter to collect the solid and wash the solid with water (2×200 mL). Slurry the solid in 300 mL of water at 25° C. for 1 h, filter and wash the solid with water (2×100 mL). Dry the solid under vacuum at 45°–50° C. for 16 h to give 87 g of the product.

Step (b):

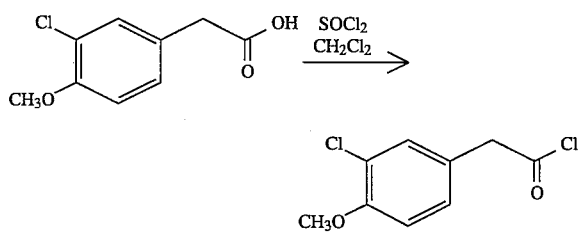

Combine 140 g of the product of Step (a) and 140 mL of $CH_2Cl_2$ at room temperature. Stir the mixture and slowly add (dropwise) 61.2 mL of $SOCl_2$, then heat the mixture to 65° C. for 1 h. Distill under vacuum to remove the solvent, then add 25 mL of toluene and continue distillation. Add 25 mL of toluene and again distill to give a final volume of 110 mL of the title compound as a 6.35M solution.

EXAMPLE 1

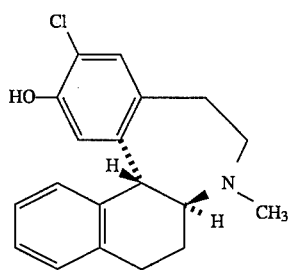

Step (a):

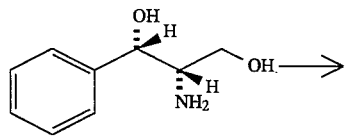

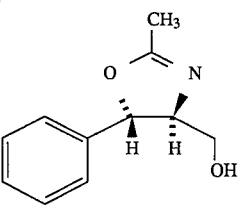

Combine
Step (b):

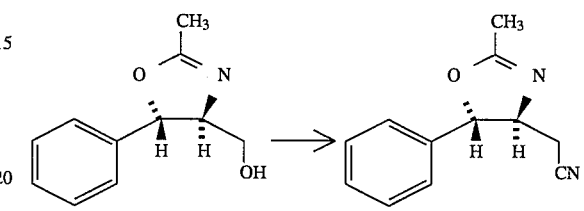

Combine the product of step (a) (100 g, 0.513 mol) and 200 mL of toluene, add 87 mL (0.625 mol) of $Et_3N$, then cool to 10° C. Slowly add (dropwise) 48.7 mL (0.625 mol) of mesyl chloride, keeping the temperature <35° C. Stir the mixture at 25° C. for 1 h, then slowly add 200 mL of saturated $NaHCO_3$ (aqueous). Filter, wash the filter cake with 100 mL of EtOAc, then extract the flitrate with the EtOAc wash. Extract the aqueous layer with 2×100 mL of EtOAc. Combine the extracts, wash with brine (2×50 mL), dry over $K_2CO_3$, filter, then concentrate in vacuo to a slurry. In a separate vessel combine 500 mL of DMSO and 64 g (1.31 mol) of NaCN and heat the mixture to 70° C. Slowly add the slurry and heat at 75° to 80° C. for 9 h. Cool the mixture to 25° C., then pour the mixture into 600 mL of saturated $NaHCO_3$ (aqueous). Add 600 mL of water and extract with EtOAc (3×300 mL). Combine the extracts, wash with $NaHCO_3$ (2×200 mL) and concentrate in vacuo to give 103 g of the oxazoline product. $^1$H NMR ($CDCl_3$, ppm): 7.27–7.43 (m, 5H); 5.21 (d, J=6.6 Hz, 1H); 4.19 (d of d, J=6.6, 6.0 Hz, 1H); 2.71 (d, J=6.0 Hz, 2H); 2.14 (d, J=1 Hz, 3H). $^{13}$C NMR ($CDCl_3$, ppm): 166.2; 138.8; 128.8; 125.2; 116.6; 84.8; 70.5; 40.7; 23.7; 13.7.

Step (c):

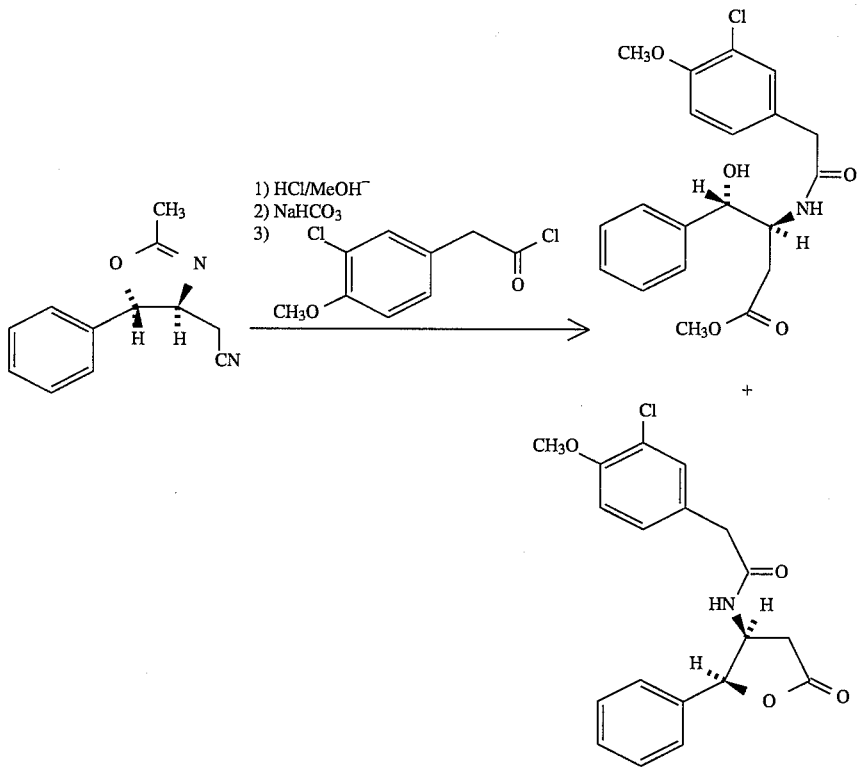

Combine the product of step (b) (50 g, 238 mmol) and 100 mL of concentrated HCl and heat the mixture at 75° C. for 2 h. Distill the mixture at 75° C. under vacuum to form a slurry. Add 50 mL of toluene distill, then add 50 mL of toluene and redistill to remove water from the slurry. Add 200 mL of MeOH, cool the mixture to 10° C. then bubble HCl gas into the mixture for 30 min. Stir the mixture at 25° C. for 16 h, then concentrate in vacuo at 37° C. to a volume of 50 mL. Add 50 mL of THF and cool the mixture to 10° C. Add 400 mL of saturated $NaHCO_3$ (aqueous) to adjust to pH 7. Distill the mixture under vacuum at <40° C., add 50 mL of THF and continue distillation to remove residual MeOH. Cool the mixture to 15° C. and add 20 g of $K_2CO_3$ to adjust to pH 8.5. Slowly add (dropwise) 40 mL of the 6.35M solution of the acid chloride of Preparation 1. Maintain pH at 7.5–8.5 by addition of 25 g $K_2CO_3$ during the acid chloride addition. Stir the mixture at 20°–25° C. for 1 h, then filter to collect the resulting precipitate. Wash the precipitate with water (2×200 mL), then dry under vacuum at 50° C. for 16 h to give 70 g of the product as a 73:27 to 75:25 mixture of the amide and the lactone. For the amide product; $^1H$ NMR ($CDCl_3$, ppm): 7.18–7.33 (m, 5 H); 6.98 (d of d, J=8.3, 1.8 Hz, 1H); 6.19 (d, J=8.3 Hz, 1H); 5.66 (d, J=6.0 Hz, 1H); 4.83 (d, J=4.3 Hz, 1H); 4.32–4.37 (m, 1H); 3.88 (s, 3H); 3.62 (s, 3H); 3.34 (s, 2H); 2.69 (d of d, J=16.1,6.0 Hz, 1H); 2.55 (d of d, J=16.1, 6.6 Hz, 1H).

For the lactone product; $^1H$ NMR ($CDC_3$, ppm): 7.26–7.39 (m, 3H); 7.10–7.14 (m, 2H); 6.81 (s, 1H); 6.73 (s, 2H); 5.69 (d, J=6.0 Hz, 1H); 4.94–5.00 (m, 1H); 3.90 (s, 3H); 3.23 (s, 2H); 3.00 (d of d, J=18.0, 7.5 Hz, 1H); 2.67 (d of d, J=18.0, 3.6 Hz, 1H).

Step (d):

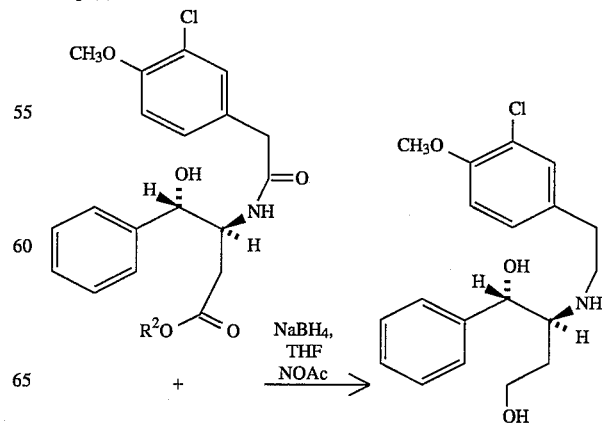

-continued

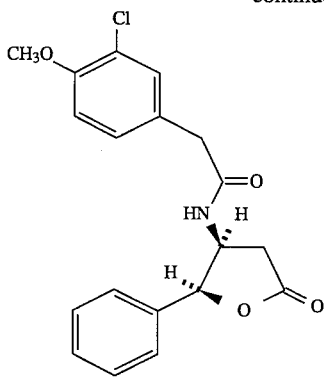

Combine the product mixture of step (c) (50 g, 0.129 mole), 40 g (1.03 mole) of NaBH₄ and 400 mL of THF at room temperature. Heat the mixture at reflux for 2 h, then cool to 10° C. and slowly add (dropwise) 51 mL of HOAc. Heat the mixture at reflux to complete the reduction, then cool to 10° C. and slowly add (dropwise) 500 mL of water. Add 50 g of 50% NaOH to adjust to pH 12, then concentrate in vacuo at 50° C. to remove the THF. Add 250 mL of EtOAc, stir for 15 min, then filter and wash the solids with EtOAc. Extract the aqueous portion of the flitrate with EtOAc (2×250 mL), combine the EtOAc extracts and the EtOAc portion of the flitrate and wash with dilute NaOH (aqueous) (2×100 mL). Dry over K₂CO₃, filter, and concentrate in vacuo to give 47 g of the diol product.
¹H NMR (CDCl₃, ppm): 7.26–7.40 (m, 5H); 7.19 (d, J=1.4 Hz, 1H); 7.04 (d of d, J=8.3, 1.4 Hz, 1H); 6.85 (d, J=8.3 Hz, 1H); 4.61 (d, J=7.1 Hz, 1H); 3.88 (s, 3H); 3.55–3.85 (m, 2H); 2.65-3.30 (m, 8H); 1.60–1.75 (m, 1H); 1.45–1.60 (m, 1H).

Step (e):

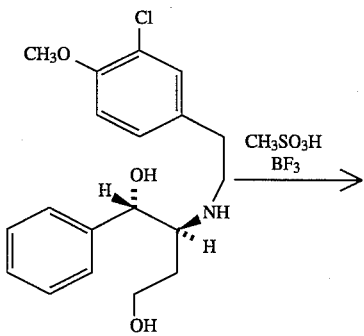

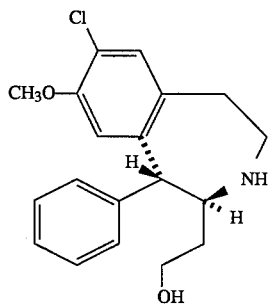

Combine the product of step (d) (20 g, 51.5 mmol) and 80 mL of CH₃SO₃H, cool to 10° C. and bubble BF₃ through the mixture for 30 min (keep the temperature under 20° C.). Slowly add the mixture to 200 mL of water and 110 g of 50% NaOH at 10° C. (Maintain a pH of 10–13 by adding more NaOH as necessary.) Stir the mixture for 2 h at 10° C., then filter to collect the solid. Wash the solid with brine (2×200 mL), then dry briefly at 50° C to give the product. ¹H NMR (CDCl₃, ppm): 7.22–7.36 (m, 3H); 7.15 (s, 1H); 7.09–7.16 (m, 2H); 6.57 (s, 1H); 3.99 (d, J=6.3 Hz, 1H); 3.77 (s, 3H); 3.72-3.85 (m, 1H); 3.55-3.70 (m, 1H); 2.85–3.15 (m, 4H); 2.60–2.75 (m, 1H); 1.80–2.00 (m, 1H); 1.57 (d of d, J=14.7, 2.7 Hz, 1H).

Step (f):

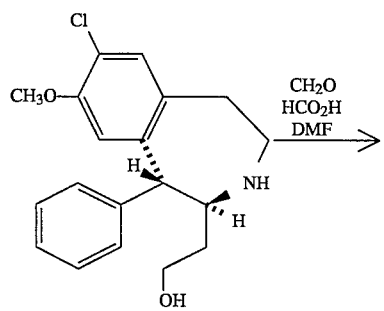

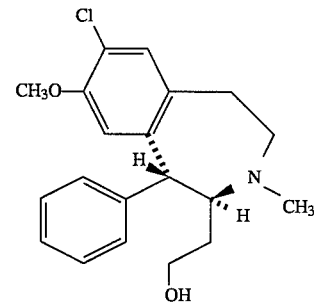

Combine the product of step (e) (26 g, 78 mmol) and 208 mL of DMF, then add 11.6 mL (155 mmol) of 37% aqueous formaldehyde and 12.2 mL (3.12 mol) of formic acid, and heat the mixture at 100° C. for 2 h. Cool the mixture to 10° C. and add 100 mL of MeOH. Add 25 g of 50% NaOH to adjust to pH 12–13, then heat the mixture to 65° C for 3 h. Add NaOH as necessary to adjust the pH at 10–12, then cool the mixture to 15° C. and add 400 mL of water. Stir the mixture at 25° C. for 16 h, then filter to collect the resulting precipitate. Wash the solid with water (2×100 mL), slurry in 400 mL of water for 2 h, filter, wash the solid with water (2×200 mL) and dry under vacuum at 50° C. for 16 h to give 32.6 g of the product. ¹H NMR (CDCl₃, ppm): 7.15–7.45 (m, 6H); 6.55 (s, 1H); 4.07 (d, J=6.5 Hz, 1H); 3.77 (s, 3H); 3.65–3.85 (m, 3H); 2.85–3.45 (m, 3H); 2.57 (d of m, J=16.0 Hz, 1H); 2.25 (s, 3H); 1.85–2.00 (m, 1H); 1.43 (d of m, J=10.9 Hz, 1H).

23

Step (g):

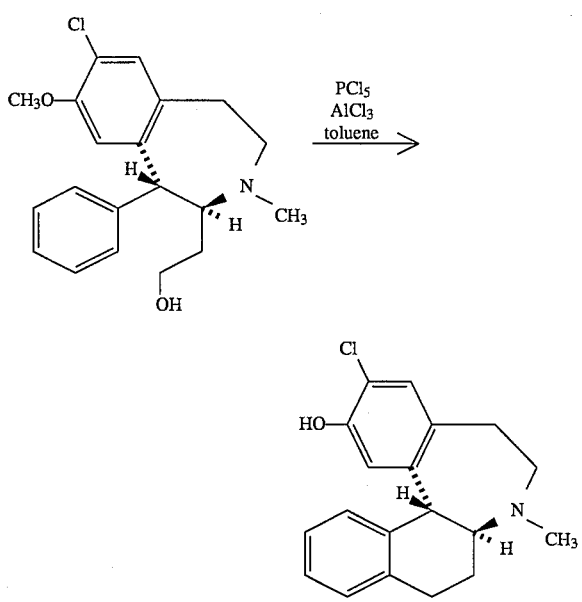

Combine the product of step (f) (10 g, 28.4 mmol) and 50 mL of toluene, then add 2.9 g (13.9 mmol) of PCl₅ and heat the mixture at 65° C. for 1 h. Cool the mixture to 25° C., slowly add 11.5 g (84.4 mmol) of AlCl₃, then heat the mixture to 65° C. for 5 h. Cool to 25° C. then add 10 mL of CH₃CN and continue stirring. Combine 150 mL of 4.0N NaOH, 35 g of malic acid and 10 mL of CH₃CN in a separate vessel, then heat this mixture to 40° C. Slowly add (dropwise) the original reaction mixture to the malic acid mixture, maintaining the pH at 9–10 by adding 50% NaOH as needed. Reduce the total volume to 200 mL by heating at 45° C. under vacuum. Filter and wash the solid with the flitrate, then wash the solid with water (2×20 mL). Slurry the solid at 40° C. in 50 mL of NaOH (aqueous) containing 2 g of malic acid, adding 50% NaOH as needed to maintain pH at 9–10. Filter and wash the solid with the flitrate, then wash the solid with water (2×20 mL). Dry the solid at 50° C. under vacuum for 16 h to give 7.41 g of the product as the free base.

Combine 5 g of the free base and 14 mL of a 1.25N solution of HCl in MeOH. Heat the mixture to reflux to dissolve the solid, then add 1 g of Darco® and 1 g of Celite® and continue to heat for 15 min. Filter the hot solution through Celite®, wash the filter cake with hot MeOH (2×10 mL), then combine the tiltrate and washings and concentrate to a volume of 3 mL. Cool the resulting slurry to 25° C., add 3 mL of t-BuOMe and stir the mixture at 10° C. for 30 min. Filter to collect the solid, wash the solid with the flitrate, then wash the solid with a cold 1:1 mixture of MeOH and t-BuOMe (2×2 mL). Dry the solid at 50° C. under vacuum for 16 h to give 4.9 g of the title compound as the HCl salt. Recrystallize from MeOH/t-BuOMe to give the title compound having an optical purity of 99.7% e.e.

24

The optical purity of the title compound is determined by chiral HPLC (Synchropak® C-4-300Å column, mobile phase: 96:4:0.8 water/CH₃CN/Et₃N containing β-cyclodextrin adjusted to pH=4.5 with HOAc.)

EXAMPLE 2

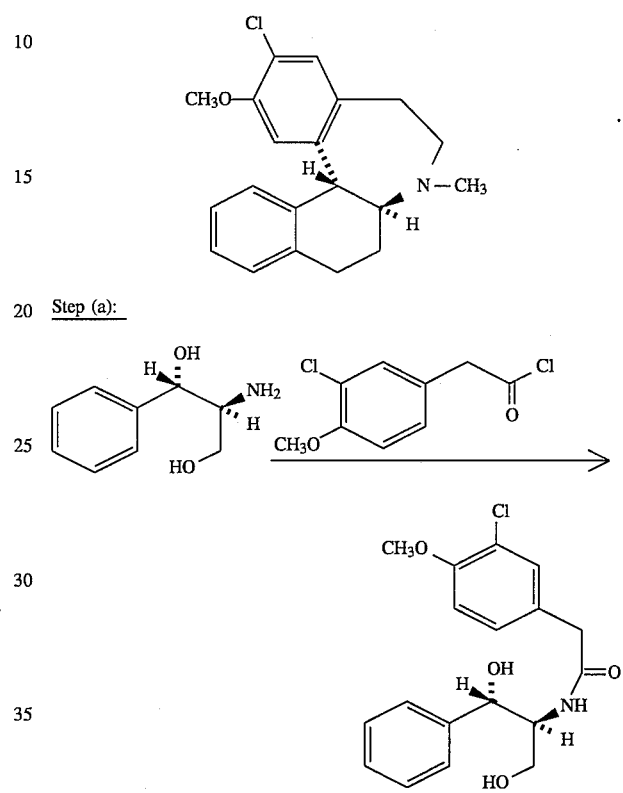

Step (a):

Combine the chiral amino diol (50 g, 0.293 mole), 500 mL of water and 93.76 g (1.172 mole) of 50% NaOH. Heat the mixture to 50° C. to form a homogeneous mixture, then cool to room temperature. Cool the mixture to 20° C., then slowly adding (dropwise) a mixture of an excess (about 0.4 mole) of the acid chloride of Preparation 1 and 50 mL of CH₂Cl₂. Maintain the reaction mixture at 18°–25° C. during the addition. Rinse with 2×10 mL of CH₂Cl₂ to ensure complete transfer of the acid chloride solution. Stir the mixture at 20° C. for about 2.5 h, then add 200 mL of MeOH and stir at 25° C. for 16 h. Concentrate in vacuo at 45° C., stir the concentrated mixture at 0°–10° C. for 30 min, then filter to collect the solid. Slurry the solid with water and 1.0N NaOH, filter, then dry the solid in vacuo at 50° C. to give 100.4 g of the product. ¹H NMR (DMSO-d6): 7.64 (d, J=8.7 Hz, 1H); 7.18–7.25 (m, 6H); 6.97–7.01 (m, 2H); 5.52 (d, J=4.3 Hz, 1H); 4.86 (m, 1H); 4.78 (t, J=5.4 Hz, 1H); 3.86 (br s, 1H); 3.81 (s, 3H); 3.20–3.62 (m, 4H).

¹³C NMR (DMSO-d6): 172.5; 155.3; 145.6; 132.0; 131.6; 130.6; 129.3; 128.3; 127.9; 122.1; 113.9; 70.2; 61.0; 56.8;

56.4; 40.9.

Step (b):

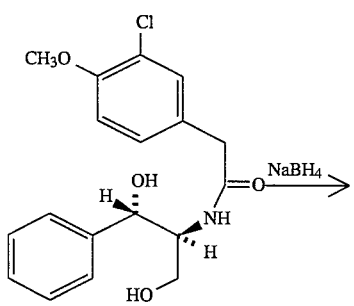

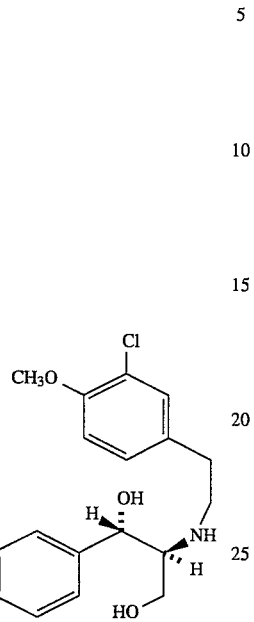

Combine the product of Step (a) (0.5 g, 1.4 mmol) and 5 mL of THF, then add 0.27 g (7.1 mmol) of NaBH₄. Cool the mixture to 10° C., then slowly add (dropwise) a solution of 0.43 g (7.1 mmol) of AcOH in 2 mL of THF over a period of 5 min. Heat the resulting mixture at reflux for 7 h., then add 0.1 g of NaBH and 0.168 g of AcOH, and continue heating at reflux for 3 h. Cool the mixture to 5° C., slowly add (dropwise) 2 mL of water, then quench the mixture into 10 mL of brine. Adjust the pH to 10 with NaOH, then extract with EtOAc (4×10 mL). Combine the extracts and wash with 5 mL of brine (containing NaOH to bring the pH to 10). Dry the organic extracts over K₂CO₃, filter and concentrate in vacuo to give 0.46 g of the product.

¹H NMR (CDCl₃): 7.25–7.45 (m, 5H); 7.16 (d, J=2.0 Hz, 1H); 7.00 (d of d, J=8.3, 2.0 Hz, 1H); 6.83 (d, J=8.3 Hz, 1H); 4.59 (d, J=7.2 Hz, 1H); 3.87 (s, 3H); 3.60 (d of d, J=11.2, 3.9 Hz, 1H); 3.36 (d of d, J=11.2, 3.9 Hz, 1H); 2.67–2.97 (m, 8H).

¹³CNMR(CDCl₃): 155.2; 143.1; 133.9; 131.4; 129.5; 128.9; 127.4; 123.2; 112.8; 73.2; 64.7; 59.7; 55.7; 48.1; 34.6; 12.9.

Step (c):

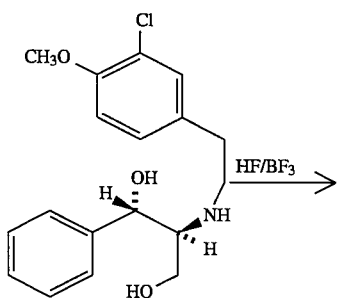

Step (c):

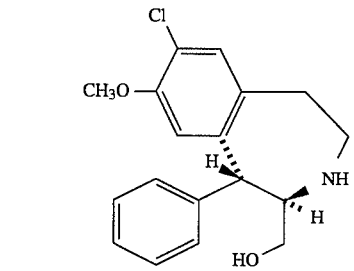

Place the product of Step (b) (4.1 g, 12.2 mmol) in a plastic vessel, cool to −78° C., then add 40 mL of HF (liquid). (Appropriate protective measures should be taken when handling HF.) Gently bubble BF₃ gas into the mixture, maintaining the temperature at −78° to −30° C. for 5 h. Allow the mixture to warm to −10° C. and evaporate the HF and excess BF₃, then cool to −20° C. and add 25 mL of CH₂Cl₂ and stir for 3 h. Warm the mixture to room temperature, stir for 2 h, then cool to −20° C. and cautiously add (dropwise) 40 mL of water. Add ice to bring the volume to 250 mL, then cautiously add 50% NaOH (aqueous) to adjust pH to 12. Allow the mixture to stand at room temperature for 16 h, then add 250 mL of EtOAc. Filter the mixture, separate the flitrate and wash the solids with 200 mL of EtOAc. Extract the aqueous portion of the flitrate with EtOAc (3×150 mL), then combine all the organic portions and wash with a solution of 2 g NaOH in brine (2×50 mL). Dry the organic portions over MgSO₄, filter, then concentrate the flitrate in vacuo to give 3.5 g of the product. ¹H NMR (CDCl₃): 7.0–7.38 (m, 6H); 7.09 (s, 1H); 3.96 (d, J=6.2 Hz, 1H); 3.74 (s, 3H); 3.55–3.68 (m, 1H); 3.35–3.52 (m, 2H); 2.70–3.15 (m, 5H); 2.50–2.70 (m, 1H).

¹³C NMR (CDCl₃): 155.0; 142.4; 140.9; 132.4; 129.7; 128.7; 127.6; 121.0; 115.6; 110.9; 62.5; 59.3; 55.5; 54.0; 42.0; 34.2.

Step (d):

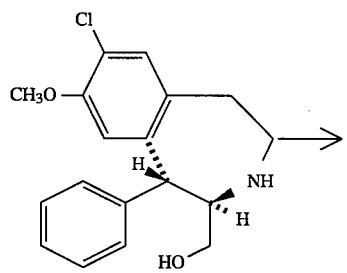

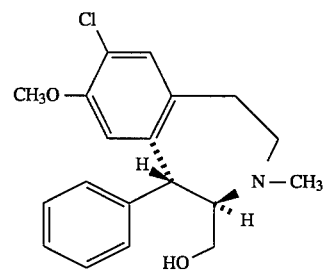

Combine 3.5 g (11 mmol) of the product of Step (c) and 14 mL of DMF at room temperature, then add 1.69 mL (22 mmol) of formaldehyde and 2.09 g (44 mmol) of formic acid, and warm the mixture to 45° C. Heat the mixture to 115° C. for 4.5 h, then cool to –5° C. Add a solution of 3.5 g of 50% NaOH in 3 mL of water to adjust the pH to 10.5. Filter to remove insoluble solids and wash the solids with EtOAc. Extract the flitrate with EtOAc (3×25 mL), combine the EtOAc wash and extracts, then wash the organic solution with water (2×10 mL) containing 1 g of Na₂CO₃. Dry over Na₂CO₃, filter, wash the solid with EtOAc, combine the flitrate and wash solution and concentrate in vacuo to give 3.5 g of the crude product. Chromatograph the crude product (silica gel, solvent gradient: hexane; hexane+NH₄OH; 1:1 hexane/EtOAc+NH₄OH; 1:2 hexane/EtOAc+NH₄OH; EtOAc+NH₄OH; EtOAc/MeOH+NH₄OH) to give 1.16 g of the product.

¹H NMR (CDCl₃): 7.14–7.34 (m, 6H); 6.55 (s, 1H); 3.76 (s, 3H); 3.52–3.72 (m, 1H); 3.51 (s, 1H); 3.50 (d of d, J=6.8, 1.1 Hz, 1H); 2.85– 3.22 (m, 5H); 2.60 (d of m, J=14.9 Hz, 1H); 2.29 (s, 3H).

Step (e):

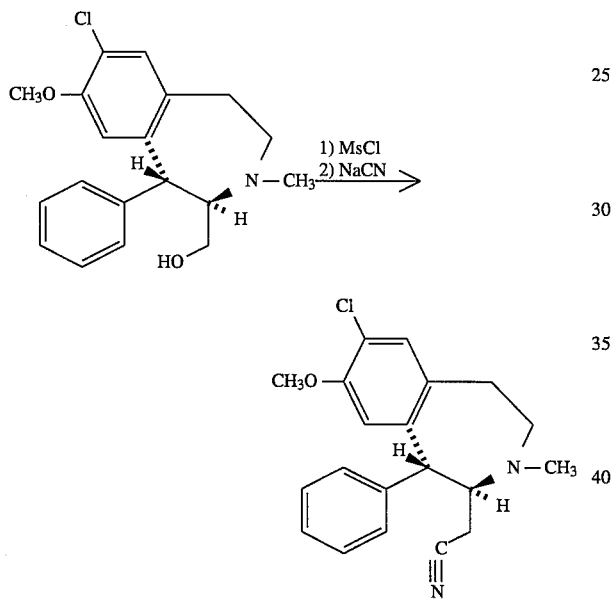

Combine 1.0 g (3.0 mmol) of the product of Step (d) and 4 mL of THF, then add 0.5 mL (3.6 mmol) of Et₃N and cool the mixture to 5° C. Add 0.28 mL (3.6 mmol) of mesyl chloride and stir the mixture at 5° C. for 1 h. Add 1 mL of water, concentrate in vacuo to a residue, then treat the residue with 10 mL of saturated NaHCO₃ (aqueous). Add 1.0N NaOH (aqueous) to adjust the pH to 10, then extract with EtOAc (5×10 mL). Combine the extracts, wash with saturated NaHCO₃ (2×5 mL), then dry the combined extracts over K₂CO₃. Filter and concentrate in vacuo to give 0.96 g of the mesylate intermediate.

Combine 0.13 g (2.6 mmol) of NaCN and 3 mL of DMSO, then heat the mixture to 70° C. Slowly add (dropwise) a solution of 0.9 g (2.2 mmol) of the mesylate intermediate in 1 mL of toluene, to the 70° C. mixture, using another 1 mL of toluene to rinse. Heat the mixture at 70° C. for 1.5 h, then cool to 25° C. and add 1 mL of water followed by 10 mL of saturated NaHCO₃ (aqueous). Extract with EtOAc (5×10 mL), combine the extracts, dry over K₂CO₃, filter and concentrate in vacuo to give 0.96 g of the crude product. Slurry the crude product in 3 mL of MeOH, filter and wash the solid with MeOH (2×1 mL). Dry the solid under vacuum at 45° C. for 16 h to give 0.5 g of the product.

¹H NMR (CDCl₃): 7.10–7.33 (m, 5H); 7.14 (s, 1H); 6.87 (s, 1H); 4.48 (d, J=5.0 Hz, 1H); 4.02–4.10 (m, 1H); 3.91 (s, 3H); 2.45 (s, 3H); 2.35–2.82 (m, 5H); 2.18 (d of d, J=10.3, 10.1 Hz). ¹³C NMR (CDCl₃): 156.6; 142.4; 140.4; 136.5; 134.5; 130.9; 130.2; 128.9; 123.2; 121.6; 118.6; 62.2; 57.5; 55.1; 49.9; 46.5; 35.2; 13.6.

Step (f):

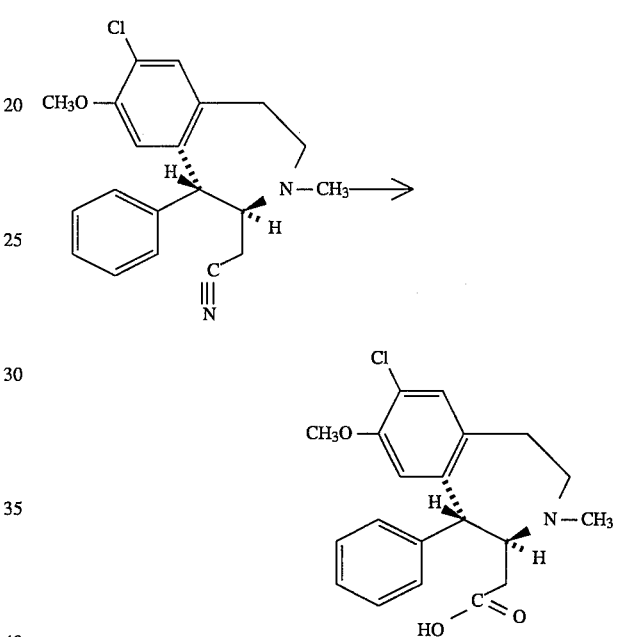

Combine 0.5 g (1.46 mmol) of the product of Step (e), 1 mL of MeOH, 0.5 mL of H₂SO₄ and 0.5 mL of water and heat the mixture to 60°–70° C. for 3 h. Add 1 mL of concentrated HCl and heat for about 20 h. Cool the mixture to room temperature and stir overnight. Add a small amount of water and adjust to pH 4 by adding 50% NaOH. Extract with EtOAc (4×25 mL), combine the extracts and concentrate in vacuo to a residue. Dissolve the residue in 4 mL of 4.0N H₂SO₄ (aqueous), stir at room temperature overnight, then heat to 50° C. for 46 h. Cool the mixture to room temperature, add ice and 10 mL of water, then adjust to pH 4 by adding 50% NaOH. Saturate the mixture with NaCl then extract with EtOAc (4×25 mL). Combine the extracts, wash with 25 mL of a pH 4 solution of H₂SO₄ in water. Concentrate the combined extracts in vacuo to give 0.56 g of the product. ¹H NMR (CDCl₃): 7.13 (s, 1H); 7.03–7.28 (m, 5H); 6.63 (s, 1H); 4.03–4.16 (m, 2H); 3.74 (s, 3H); 3.04–3.17 (m, 1H); 2.84–2.85 (m, 1H); 2.28 (s, 3H); 2.15–2.53 (m, 3H). ¹³C NMR (CDCl₃): 177.8; 155.2; 141.4; 139.2; 133.5; 132.7; 129.5; 128.7; 127.6; 121.4; 116.6; 60.9; 55.6; 54.7; 48.4; 42.0; 32.8; 31.0.

Step (g):

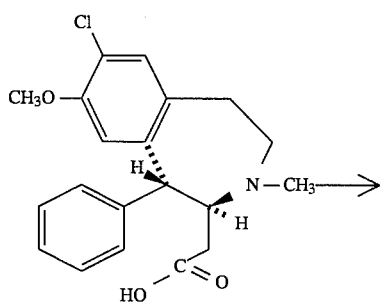

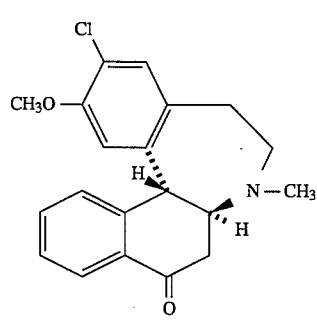

Combine 2.0 g (5.6 mmol) of the product of Step (f) and 11.2 mL (153 mmol) of SOCl₂ and heat the mixture to 40° C. for 15 min. Remove the excess SOCl₂ by distillation, add 10 mL of CH₂Cl₂ and distill again to a residue. Add 10 mL of CH₂Cl₂ to the residue and cool to 5° C., then add 2.24 g (16.8 mmol) of AlCl₃ and stir for 15 min at 5° C. Add 50 mL of ice water, filter, wash the solids with water and dry under vacuum at room temperature to give 2.0 g of the product. ¹H NMR (CDCl₃): 7.95 (d, J=7.1 Hz, 1H); 7.60 (d of d, J=7.4, 7.1 Hz, 1H); 7.47 (d of d, J=7.7, 7.4 Hz, 1H); 7.23 (s, 1H); 7.17 (d, J=7.7 Hz, 1H); 5.87 (s, 1H); 5.85 (d, J= 9.5 Hz, 1H); 4.25 (d of d, J=13.2, 12.5 Hz, 1H); 3.80–3.95 (m, 1H); 3.64 (d, J=13.2 Hz, 1H); 3.54 (d, J=13.2 Hz, 1H); 3.48 (s, 3H); 3.40–3.55 (m ,1 H); 3.15 (d of d, J=12.5, 4.4 Hz, 1H); 2.87 (d, J=4.7 Hz, 3H); 2.80–3.05 (m, 2H).

Step (h):

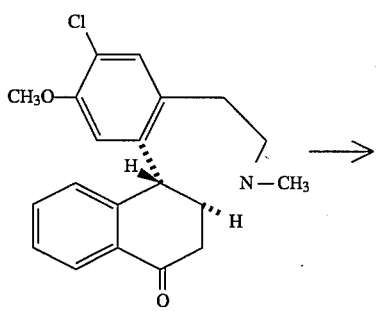

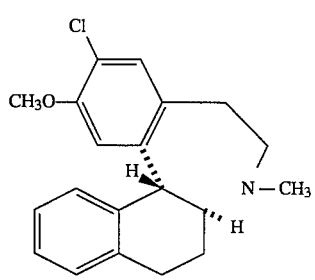

Combine 0.1 g (0.265 mmol) of the product of Step (g) and 2 mL of CF₃CO₂H and stir the mixture for 5 min. Add 0.08 mL of 10M BH₃. S(CH₃)₂ and stir the mixture at room temperature for 30 min. Cool the mixture to 5° C. and slowly add (dropwise) 4 mL of water, then add 50% NaOH to adjust to pH 12. Extract with EtOAc (4×10 mL), combine the extracts, dry over K₂CO₃, filter and concentrate in vacuo to give 0.5 g of the title compound. ¹H NMR (CDCl₃): 7.12–7.20 (m, 3H); 7.12 (s, 1H); 6.95–7.02 (m, 1H); 5.89 (s, 1H); 4.79 (d, J=7.1 Hz, 1H); 3.50–3.62 (m, 1H); 3.49 (s, 3H); 3.22 (d of d, J=12.0, 4.0 Hz, 1H); 2.60–2.90 (m, 4H); 2.54 (s, 3H); 2.45 (d of d, J=15.1, 5.2 Hz, 1H); 2.02–2.15 (m, 1H); 1.72 (d of d, J=12.2, 4.6 Hz, 1H).

¹³C NMR (CDCl₃): 153.0; 148.0; 139.3; 139.2; 137.2; 134.7; 131.1; 130.0; 128.1; 126.1; 118.7; 111.1; 66.5; 58.2; 55.8; 44.9; 37.5; 31.9; 29.6.

The methoxy group of the product of Example 2, Step (h), is hydrolyzed by treating with BCl₃ or via the prior art procedure described above to give SCH 39166.

EXAMPLE 3

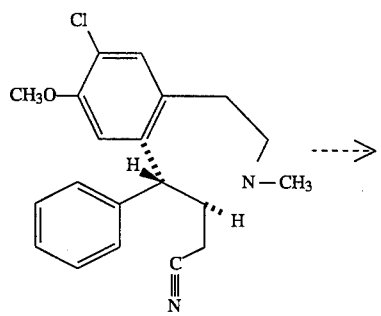

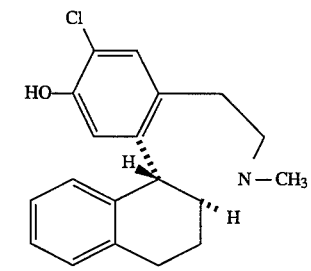

Step (a):

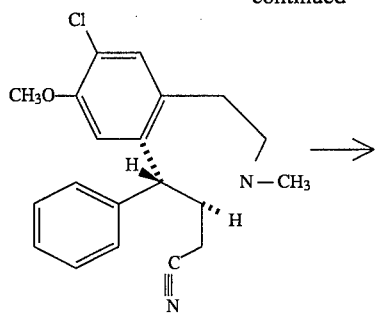

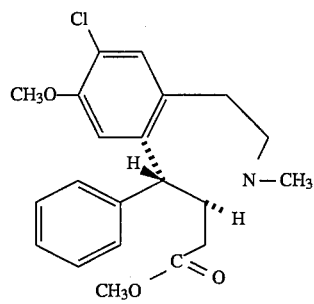

Combine 2.0 g (5.9 mmol) of the product of Example 2, Step (e), 19 mL of MeOH and 1 mL of water, and stir the mixture at room temperature. Slowly add (dropwise) 8 mL of H$_2$SO$_4$, then heat the mixture to 65° C. for 4 days. Cool the mixture to 0° C., add 50% NaOH to adjust to pH 12, and filter to collect the solid precipitate. Wash the solid with water and dry the solid at 45° C. overnight. Slurry the solid in water (2×50 mL) then fry at room temperature for 2 days to give 1.95 g of the product. $^1$H NMR (CDCl$_3$): 7.10–7.30 (m, 5H); 7.13 (s, 1H); 6.64 (s, 1H); 4.22 (br s, 1H); 4.12 (d of d, J=14.0, 6.0 Hz, 1H); 3.84 (s, 3H); 3.66 (s, 3H); 2.70–2.90 (m, 1H); 2.39–2.70 (m, 4H); 2.39 (s, 3H); 2.20 (d of d, 14.9, 9.3 Hz, 1H).

Step (b):

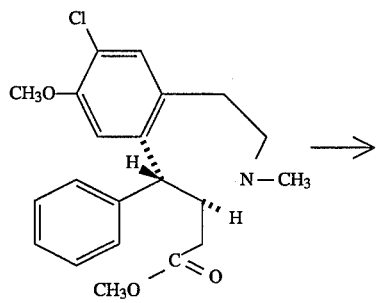

Step (b):

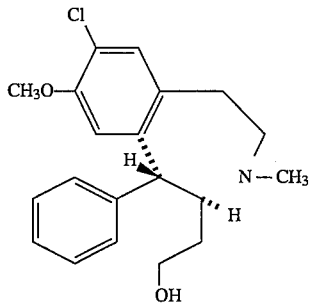

Combine 0.8 g (2.08 mmol) of the product of Step (a) and 2 mL of MeOH, then cool the mixture to 10° C. Add 0.24 g (6.2 mmol) of NaBH$_4$, then slowly add (dropwise) a solution of 0.35 g (3.2 mmol) of anhydrous CaCl$_2$ in MeOH. Allow the mixture to warm to room temperature for 30 min, then heat to 45° C. for 2 h. Remove the MeOH under vacuum and add 2 mL of THF. Add 0.24 g of NaBH$_4$ and 0.26 g of LiCl, then stir at room temperature for 1 h, then heat to 80° C. for 2 days. Cool to 10° C. and slowly add (dropwise) 5 mL of water, then add 50% NaOH to adjust to pH 12. Extract with EtOAc (1×20 mL, 2×10 mL), combine the extracts, wash with 5 mL of NaOH in water (pH =12), then dry the extracts over K$_2$CO$_3$. Concentrate in vacuo, then crystallize from EtOAc/hexane to give a solid. Dry the solid for 2 days at room temperature to give 0.48 g of the product.

The product of Step (b) is converted to the title compound by the procedures described in Example 1, Steps (f)–(g).

We claim:

1. A process for preparing a chiral compound of the formula (I)

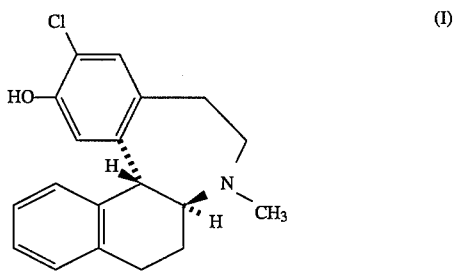

comprising the steps:

(a) regioselectively cyclizing a chiral alcohol of the formula

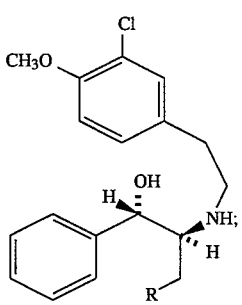

wherein R is —OH or —CH$_2$OH, by treating with CH$_3$SO$_3$H/BF$_3$, HF/BF$_3$ or TFA, to form a compound of the formula

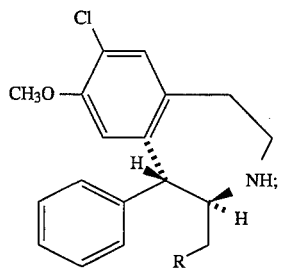

(b) treating the product of Step (a) with formaldehyde and formic acid to form an N-methyl compound of the formula

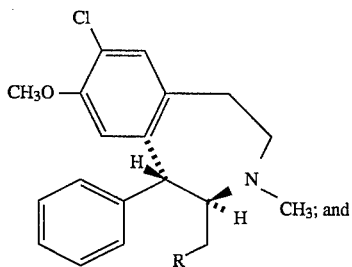

(c) where R is —CH$_2$OH, reacting the product of step (b) with PCl$_5$ and AlCl$_3$; or where R is —OH, converting the product of step (b) to the one carbon homologous product, wherein R is —CH$_2$OH or —CO$_2$H, then:

(i) where R is —CH$_2$OH, reacting the homologous product with PCl$_5$ and AlCl$_3$; or (ii) where R is —CO$_2$H, treating the homologous product with an acid activating agent and a Lewis acid to form a ketone of the formula

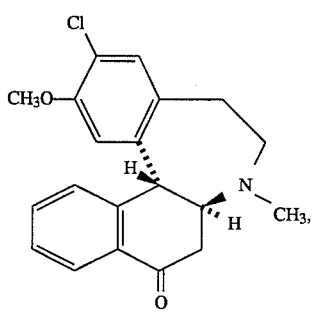

treating the ketone with a hydride reducing agent or a borane reducing agent to form a compound of formula (II)

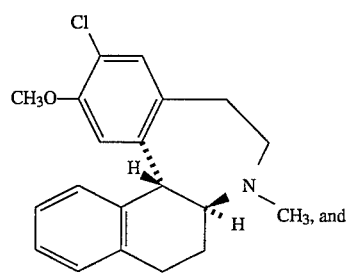

hydrolyzing the compound of formula (II); to form the compound of formula (I).

2. A process according to claim 1 wherein R is —CH$_2$OH and the chiral alcohol of step (a) is prepared by a process comprising the steps:

(A1) treating an (S,S)-amino diol of the formula

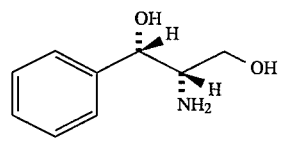

with a nitrile of the formula R$^1$CN, wherein R$^1$ is C$_1$-C$_6$ alkyl, to form a chiral oxazoline of the formula

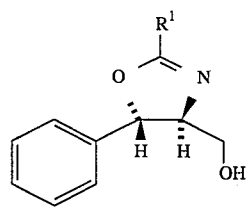

wherein R$^1$ is as defined above;

(A2) treating the chiral oxazoline of step (A1) with an activating agent, then with a cyanide salt to form a nitrile of the formula

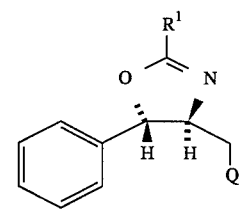

wherein R$^1$ is as defined above and Q is CN;

(A3) treating the nitrile of step (A2) with HCl and an alcohol of the formula R$^2$OH, wherein R$^2$ is C$_1$-C$_6$ alkyl, to form an ester of the formula

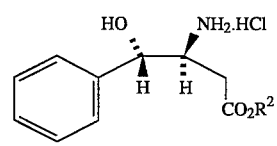

then treating the ester with a base and an acid halide of the formula

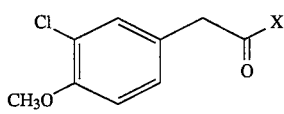

wherein X is Cl or Br, to form a mixture of an ester and a lactone of the formulae

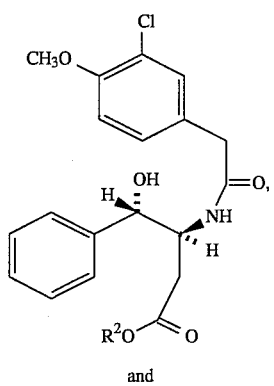

and

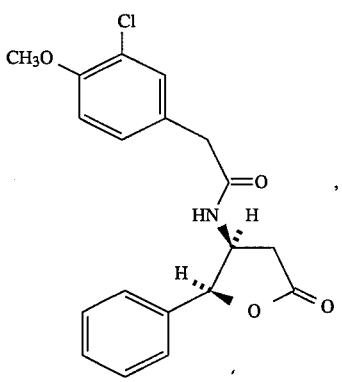

respectively, wherein R² is as defined above; and (A4) treating the ester and lactone mixture of step (A3) with a hydride reducing agent to form the chiral alcohol of step (a), wherein R is —CH₂OH.

3. A process according to claim 1 wherein R is —OH and the chiral alcohol of step (a) is prepared by a process comprising the steps:

(B1) coupling an (S,S)-amino diol of the formula

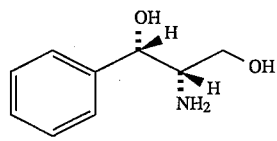

with an acid of the formula

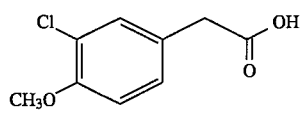

to form an amide of the formula

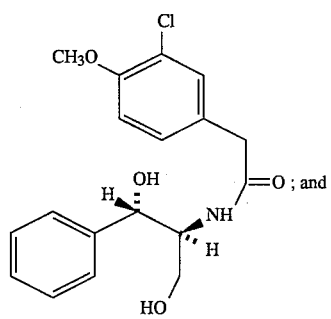

(B2) treating the amide of step (B1) with a hydride reducing agent to form the chiral alcohol of step (a), wherein R is —OH.

4. A process according to claim 1 wherein in step (c) the product of step (b), wherein R is —OH, is converted to the one carbon homologous product, wherein R is —CH₂OH or —CO₂H by a process comprising the steps:

(C1) treating the product of step (b) with an activating agent to form a compound of the formula

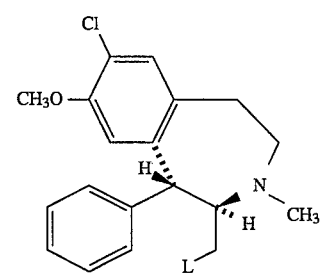

wherein L is a leaving group;

(C2) treating the product of step (C1) with a cyanide salt to form a compound of the formula

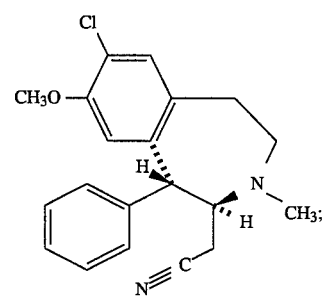

(C3) (i) treating the product of step (C2) with a strong acid and water to form the homologous product wherein R is —CO₂H; or (ii) treating the product of step (C2) with a strong acid and an alcohol of the formula R²OH to form an ester of the formula

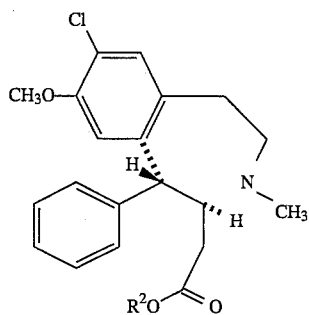

wherein $R^2$ is $C_1$-$C_6$ alkyl, and treating the ester with a hydride reducing agent to form the homologous product where R is —CH$_2$OH.

5. A process according to claim 1 wherein: R is —CH$_2$OH

6. A process according to claim 1 wherein: R is —OH; and in step (c), the product of step (b) is converted to the one carbon homologous product wherein R is —CH$_2$OH.

7. A process according to claim 1 wherein: R is —OH; and in step (c), the product of step (b) is converted to the one carbon homologous product wherein R is —CO$_2$H.

8. A process according to claim 7 wherein Step (c) (ii): the activating agent is SOCl$_2$ or oxalyl chloride; the Lewis acid is AlCl$_3$; the borane reducing agent is BH$_3$.S(CH$_3$)$_2$; and wherein compound II is hydrolyzed by treating with BCl$_3$ or with HBr and HOAc.

9. A process according to claim 2 wherein: $R^1$ is CH$_3$; the activating agent to step (A2) is mesyl chloride or tosyl chloride; the cyanide salt of step (A2) is NaCN, KCN or LiCn: $R^2$ is CH$_3$; X is Cl; and in step (A4) the hydride reducing agent is NaBH$_4$.

10. A process according to claim 3 wherein: in step (B1) the coupling of the (S,S)-amino diol to the acid is by treating the acid with an acid activating agent or the diol and acid with an amide coupling agent; and the hydride reducing agent of step (B2) is NaBH$_4$.

11. A process according to claim 10 wherein: the acid activating agent is SOCl$_2$ or oxalyl chloride; the amide coupling agent is either DCC or DEC, and is used in the presence of HOBT.

12. A process according to claim 4 wherein: the activating agent of step (C1) is mesyl chloride or tosyl chloride; L is OMs or OTs; the cyanide salt of step (C2) is NaCN, KCN or LiCN; the strong acid of step (C3) (i) is H$_2$SO$_4$; and in step (C3) (ii), the strong acid is H$_2$SO$_4$, $R^2$ is CH$_3$, and the hydride reducing agent is LiBH$_4$.

13. A chiral compound of the formula

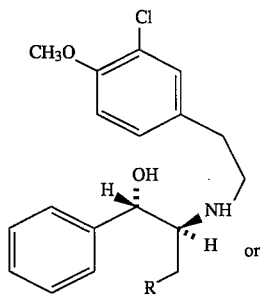

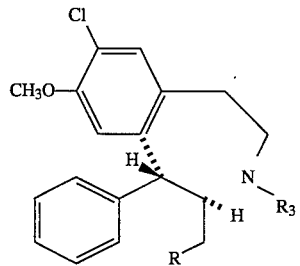

wherein R is —CH$_2$OH or —OH and $R^3$ is H or $C_1$-$C_6$ alkyl.

* * * * *